United States Patent
Suzuki et al.

(10) Patent No.: US 9,732,012 B2
(45) Date of Patent: Aug. 15, 2017

(54) METHOD FOR PRODUCING OLEFIN

(71) Applicants: Sumitomo Chemical Company, Limited, Tokyo (JP); Idemitsu Kosan Co., Ltd., Chiyoda-ku, Tokyo (JP); Tokyo Institute of Technology, Meguro-ku, Tokyo (JP)

(72) Inventors: Tetsuo Suzuki, Ichihara (JP); Takahiro Kakinuma, Ichihara (JP); Hiroshi Ohashi, Sodegaura (JP); Masakazu Iwamoto, Meguro-ku (JP)

(73) Assignees: Sumitomo Chemical Company, Limited, Tokyo (JP); Idemitsu Kosan Co., Ltd., Tokyo (JP); Tokyo Institute of Technology, Tokyo (JP)

( * ) Notice: Subject to any disclaimer, the term of this patent is extended or adjusted under 35 U.S.C. 154(b) by 0 days.

(21) Appl. No.: 14/614,700

(22) Filed: Feb. 5, 2015

(65) Prior Publication Data

US 2015/0148580 A1    May 28, 2015

Related U.S. Application Data

(62) Division of application No. 13/992,828, filed as application No. PCT/JP2011/078341 on Dec. 7, 2011.

(30) Foreign Application Priority Data

Dec. 8, 2010    (JP) ................. 2010-273663

(51) Int. Cl.
| | | |
|---|---|---|
| C07C 1/24 | (2006.01) | |
| C07C 1/20 | (2006.01) | |
| B01J 21/06 | (2006.01) | |
| C01G 25/02 | (2006.01) | |
| C07C 1/22 | (2006.01) | |

(52) U.S. Cl.
CPC ............... *C07C 1/20* (2013.01); *B01J 21/066* (2013.01); *C01G 25/02* (2013.01); *C07C 1/22* (2013.01); *C07C 1/24* (2013.01); *C07C 2521/06* (2013.01); *Y02P 20/52* (2015.11)

(58) Field of Classification Search
CPC .......... C01G 25/02; B01J 21/066; C07C 1/20; C07C 1/24; C07C 2521/06

USPC ................... 423/608; 585/640; 502/349
See application file for complete search history.

(56) References Cited

U.S. PATENT DOCUMENTS

| | | | |
|---|---|---|---|
| 5,210,363 A | 5/1993 | Sweeney | |
| 2007/0037690 A1 | 2/2007 | Fenouil et al. | |
| 2008/0103345 A1* | 5/2008 | Levin .................. | C07C 1/20 585/640 |
| 2011/0098519 A1* | 4/2011 | Ramesh et al. ............. | 585/640 |
| 2012/0220808 A1 | 8/2012 | Takada | |
| 2014/0065059 A1 | 3/2014 | Suzuki et al. | |

FOREIGN PATENT DOCUMENTS

| | | |
|---|---|---|
| JP | 02-037895 | 2/1990 |
| JP | 2008-081417 A | 4/2008 |
| JP | 2008-289991 A | 12/2008 |
| JP | 2009-018247 A | 1/2009 |
| JP | 2010-018556 A | 1/2010 |
| JP | 2010-202612 A | 9/2010 |
| WO | 2011/052732 A1 | 5/2011 |
| WO | 2012/077723 A1 | 6/2012 |

OTHER PUBLICATIONS

Song Zhaoxia et al., Production of Propylene from Ethanol Over ASM-5 Zeolites, Catal Lett, 2009.09, vol. 131, No. 3/4, pp. 364-369.
Xu et al., Fine Tuning of the Sizes and Phases of ZrO2 Nanocrystals, Oct. 8, 2009, Nano Res, 2, 891-902.
Office Action issued Sep. 23, 2014 in U.S. Appl. No. 13/992,828.
Office Action issued Nov. 5, 2014 in U.S. Appl. No. 13/992,828.
Office Action issued Sep. 15, 2015 in JP Application No. 2012547894.
Larsen et al., "Alcohol Dehydration Reactions over Tungstated Zirconia Catalysts," Journal of Catalysis, vol. 169, pp. 67-75 (1997).

* cited by examiner

*Primary Examiner* — Matthew E Hoban
*Assistant Examiner* — James Fiorito
(74) *Attorney, Agent, or Firm* — Panitch Schwarze Belisario & Nadel LLP

(57) ABSTRACT

Disclosed are a catalyst for producing, from an alcohol, an olefin whose number of carbon atoms is at least one more than the number of carbon atoms of the alcohol, wherein at least the surface of the catalyst is substantially composed of zirconium oxide; a method for producing an olefin using the same; and so on.

7 Claims, No Drawings

METHOD FOR PRODUCING OLEFIN

CROSS-REFERENCE TO RELATED APPLICATIONS

This application is a divisional of U.S. patent application Ser. No. 13/992,828, filed Nov. 22, 2013, which is a Section 371 of International Application No. PCT/JP2011/078341, filed Dec. 7, 2011, which was published in the Japanese language on Jun. 14, 2012 under International Publication No. WO 2012/077723 A1, and the disclosures of which are incorporated herein by reference.

BACKGROUND OF THE INVENTION

The present invention relates to a catalyst for producing an olefin from an alcohol and a method for producing an olefin using the catalyst. The present invention also relates to a polyolefin and an olefin oxide each of which is produced using, as a raw material, an olefin obtained by the foregoing method.

In the field of the recent production of chemical raw materials, for the purposes of suppressing the emission of carbon dioxide and preparing for drying up or a rise in prices of petroleum resources in the future, it is demanded to convert the chemical raw materials from petroleum-based resources into non-edible biomasses. In particular, there is required a technology capable of efficiently producing polypropylene that is a representative general-purpose resin, from bioethanol that is a biomass resource. As for a method for producing propylene from ethanol, for example, Non-Patent Document 1 and Patent Document 1 describe methods using a zeolite catalyst having zirconium supported thereon.

Non-Patent Document 1: *Catalysis Letters* (2009) 131: 364-369

Patent Document 1: JP-A-2010-202612

BRIEF SUMMARY OF THE INVENTION

Problem to be Solved by the Invention

However, according to the methods described in Non-Patent Document 1 and Patent Document 1, since a catalyst composed mainly of a zeolite is used, large quantities of an alkane and BTX components (e.g., benzene, toluene, and xylene) are formed as by-products, and hence, the selectivity to an olefin lowers. In consequence, the development of a technology capable of producing an olefin selectively and efficiently is eagerly demanded.

In view of the foregoing problem, the present invention has been made, and an object thereof is to provide a catalyst and a method for producing, from an alcohol, an olefin whose number of carbon atoms is more than the number of carbon atoms of the alcohol selectively and efficiently. In addition, another object of the present invention is to provide a polyolefin and an olefin oxide, each of which is produced using, as a raw material, an olefin produced by the foregoing method.

Means for Solving the Problem

In order to solve the foregoing problem, the present inventors made extensive and intensive investigations. As a result, it has been found that zirconium oxide is very effective as a catalyst component capable of producing, from an alcohol as a raw material, an olefin whose number of carbon atoms is at least one more than the number of carbon atoms of the alcohol selectively and efficiently and that at least the surface of a solid catalyst is substantially composed of zirconium oxide, leading to the accomplishment of the present invention.

Specifically, the present invention is as follows:

[1] A solid catalyst for producing, from an alcohol, an olefin whose number of carbon atoms is at least one more than the number of carbon atoms of the alcohol, wherein
  at least the surface of the catalyst is substantially composed of zirconium oxide.

[2] The catalyst as set forth in [1], wherein the whole of the catalyst is substantially composed of zirconium oxide.

[3] The catalyst as set forth in [1] or [2], wherein the alcohol is ethanol, and the olefin is propylene.

[4] The catalyst as set forth in any one of [1] to [3], wherein the zirconium oxide has a structure of either a tetragonal crystal or a cubic crystal.

[5] A method for producing an olefin including an olefin formation step of forming, from an alcohol, an olefin whose number of carbon atoms is at least one more than the number of carbon atoms of the alcohol, wherein
  in the olefin formation step, the alcohol is brought into contact with the catalyst as set forth in any one of [1] to [4] at a temperature of from 300° C. to 700° C.

[6] The method for producing an olefin as set forth in [5], wherein the alcohol contains water in an amount of not more than 7 times the molar number of the alcohol.

[7] The method for producing an olefin as set forth in [5] or [6], wherein the alcohol is brought into contact with the catalyst at a gauge pressure of 50 kPa or more.

[8] The method for producing an olefin as set forth in any one of [5] to [7], wherein the alcohol is ethanol, and the olefin is propylene.

[9] A polyolefin produced using, as a raw material, an olefin produced by the method as set forth in any one of [5] to [8].

[10] An olefin oxide produced using, as a raw material, an olefin produced by the method as set forth in any one of [5] to [8].

DETAILED DESCRIPTION OF THE INVENTION

According to the present invention, it is possible to provide a catalyst and a method capable of producing, from an alcohol, an olefin whose number of carbon atoms is at least one more than the number of carbon atoms of the alcohol selectively and efficiently. In addition, it is possible to provide a polyolefin and an olefin oxide, each of which is produced using, as a raw material, an olefin produced by the foregoing method.

MODES FOR CARRYING OUT THE INVENTION

A solid catalyst for producing an olefin of the present invention (hereinafter also referred to as "catalyst for olefin production of the present invention" or "catalyst of the present invention") and a method for producing an olefin, and also a polyolefin and an olefin oxide are described below, but the present invention is not limited to the following descriptions.

In addition, when a numerical range is expressed by the symbol "-" in the present specification, this range shall include a lower limit value and an upper limit value.

[1. Catalyst for Olefin Production]

The catalyst for olefin production of the present invention is a solid catalyst for producing, from an alcohol, an olefin whose number of carbon atoms is at least one more than the number of carbon atoms of the alcohol, wherein at least the surface of the catalyst is substantially composed of zirconium oxide.

It is meant by the terms "at least a surface is substantially composed of zirconium oxide" as referred to herein that a proportion (area ratio) of zirconium oxide on the surface is 50% by area or more. The area ratio of zirconium oxide is preferably 70% by area or more, and more preferably 100% by area (the case where the whole is zirconium oxide). It is meant by the terms "the area ratio of zirconium oxide is 100% by area" as referred to herein that the whole of the surface of the catalyst is composed of zirconium oxide.

For example, in the case where the raw material is ethanol, and the desired product is propylene, so long as only zirconium oxide exists as a reaction active catalytic species, propylene is selectively formed on the zirconium oxide from ethanol through acetone. On the other hand, in the case where there coexists another component, for example, a catalyst component having strong acidity such as a sulfate, ethylene formed by a dehydration reaction of ethanol is polymerized to form an oligomer, and a decomposition reaction in which the protonated oligomer is decomposed in various ways through skeletal isomerization and β-cleavage proceeds. Thus, the reaction according to the present invention is hindered, and various products are formed without forming mainly propylene as described above.

In consequence, it is preferable that the catalyst surface is substantially constituted of only zirconium oxide.

Examples of the form of the catalyst of the present invention include supported catalysts and oxide catalysts. A carrier of the case of the supported catalyst is not particularly limited, and examples thereof include silica, alumina, titania, magnesia, calcia, graphite, and the like. In the case where the carrier is exposed on the surface, suitable examples thereof include those having low dehydration ability against the alcohol which is used as the raw material, such as silica, α-alumina, and graphites. The loading of zirconium oxide is preferably 51% by mass or more, and more preferably 70% by mass or more. In addition, examples of the oxide catalyst include such forms as a zirconium oxide powder and a zirconium oxide molding. In the case of the zirconium oxide powder, the particle diameter thereof after sieving is preferably from 0.01 to 2 mm, and more preferably from 0.1 to 1 mm. In the case of the molding, when a rectangular parallelepiped which is circumscribed on the molding is supposed, the maximum length of the sides of the rectangular parallelepiped is preferably from 0.5 to 20 mm, and more preferably from 1 to 10 mm.

Examples of the type of the crystal structure of zirconium oxide include a tetragonal crystal, a cubic crystal, a monoclinic crystal, or an amorphous structure. Of these, the zirconium oxide which is applied to the present invention is preferably a tetragonal crystal or a cubic crystal. When the zirconium oxide is a tetragonal crystal or a cubic crystal, the selectivity to the desired olefin increases, so that the yield can be increased.

Though the alcohol which is allowed to react with the catalyst of the present invention is not particularly limited, a primary alcohol having the number of carbon atoms of from 2 to 12 is preferable. Examples of the primary alcohol having the number of carbon atoms of from 2 to 12 include ethanol, 1-propanol, 1-butanol, isobutanol, 1-pentanol, 1-hexanol, 1-heptanol, 1-octanol, 1-nonanol, 1-decanol, 1-undecanol, and 1-dodecanol. Above all, a primary alcohol having the number of carbon atoms of from 2 to 8 is preferable, and a primary alcohol having the number of carbon atoms of from 2 to 4 is more preferable. So long as the primary alcohol having the number of carbon atoms of from 2 to 12 is concerned, the selectivity to the olefin can be enhanced.

Furthermore, it is more preferable to use ethanol derived from a biological resource (biomass) as the alcohol to be applied to the present invention. Unlike the case of using ethanol obtained from a fossil fuel, the olefin can be produced without increasing carbon dioxide in the environment by using bioethanol for the reaction according to the present invention.

In addition, though the olefin to be produced varies depending upon the alcohol which is allowed to react, it is preferably propylene. In consequence, it is preferable to use the catalyst of the present invention at the time of producing propylene using ethanol as a raw material.

The method for producing the catalyst of the present invention is not particularly limited, and it is possible to apply various known production methods. Commercially available products can also be used so long as they are a material in which at least the surface thereof is substantially composed of zirconium oxide.

In the case where the catalyst of the present invention is a supported catalyst, it can be fabricated by supporting a zirconium oxide precursor on the carrier as previously described by an impregnation method or the like and then properly performing calcination (for example, at from 300 to 900° C.).

In the case where the catalyst of the present invention is an oxide catalyst, for example, it can be produced by fabricating a zirconium oxide precursor-containing precipitate, performing filtration and calcination (for example, at from 300 to 900° C.), and then properly performing sieving, molding treatment, or the like.

Here, examples of a raw material of the zirconium oxide precursor include zirconium(IV) acetylacetonate $((CH_3COCHCOCH_3)_4Zr)$, zirconium(IV) n-butoxide $(Zr(OC_4H_9)_4)$, zirconium(IV) tert-butoxide $(Zr(OC_4H_9)_4)$, zirconium(IV) n-propoxide $(Zr(OC_3H_7)_4)$, zirconium(IV) isopropoxide $(Zr(OCH(CH_3)_2)_4)$, zirconium(IV) ethoxide $(Zr(OC_2H_5)_4)$, zirconium(IV) carbonate n-hydrate $(Zr(CO_3)_2 \cdot nH_2O)$, zirconium(IV) oxide dichloride n-hydrate $(ZrCl_2O \cdot nH_2O)$, zirconium(IV) chloride $(ZrCl_4)$, zirconium (IV) bromide $(ZrBr_4)$, and zirconium(IV) dinitrate oxide n-hydrate $(ZrO(NO_3)_2 \cdot nH_2O)$.

[2. Production Method of Olefin]

The method for producing an olefin of the present invention is a method including an olefin formation step of forming, from an alcohol, an olefin whose number of carbon atoms is at least one more than the number of carbon atoms of the alcohol, wherein in the olefin formation step, the alcohol is brought into contact with the catalyst for olefin production of the present invention at a reaction temperature of from 300° C. to 700° C.

Incidentally, details of the alcohol and the olefin are those as previously described.

The alcohol which is used in the present invention preferably contains water in an amount of not more than 7 molar times the molar number of the alcohol, more preferably contains water in an amount of from 0.5 to 7 molar times the molar number of the alcohol, still more preferably contains water in an amount of from 0.5 to 6 molar times the molar number of the alcohol, and especially preferably contains water in an amount of from 1 to 5 molar times the molar number of the alcohol.

In the case where the alcohol which serves as the raw material is ethanol, examples of the olefin to be formed include propylene, 1-butene, cis-2-butene, trans-2-butene, isobutene, and pentene in addition to ethylene; and in the case where the alcohol serving as the raw material is 1-propanol, examples of the olefin to be formed include pentenes, hexenes, and octenes in addition to propylene.

Above all, the olefin to be formed is preferably propylene. In that case, in the method for producing an olefin of the present invention, it is especially preferable that propylene is selectively produced using ethanol as the raw material.

In the olefin formation step, the method for bringing the alcohol into contact with the catalyst of the present invention is not particularly limited, and it is allowable to merely introduce the alcohol into a container filled with the catalyst.

Examples of a reactor for carrying out the olefin formation step include a fixed bed reactor, a fluidized bed reactor, a batch type reactor, and a semi-batch type reactor. From the viewpoint of the productivity of the olefin, a fixed bed reactor or a fluidized bed reactor is preferable, and a fixed bed reactor is more preferable.

Though the form of the alcohol which serves as the raw material is not particularly limited, from the viewpoints of increasing the formation efficiency of an olefin and making it easy to perform the reaction, it is preferable that the alcohol is a gas at the time of contact with the catalyst.

In addition, at the time of bringing the alcohol in a gaseous state into contact with the catalyst in a container, the alcohol may also be fed in combination with other components into the container.

Examples of such other components include a nitrogen gas, water vapor, hydrogen, carbon monoxide, carbon dioxide, the entirety or part of a product recovered from an outlet of the reactor, and a carrier gas other than those described above which is substantially unreactive with the alcohol which serves as the raw material and the olefin to be formed.

Though the amount of the catalyst used is not particularly limited, it is preferably from 0.000002 tons to 0.02 tons per ton of the alcohol. In addition, the feed rate of the alcohol may be, for example, from 0.002 tons/h to 200 tons/h, and preferably from 0.02 tons/h to 20 tons/h per ton of the catalyst.

In addition, though the temperature at which the alcohol which serves as the raw material is brought into contact with the catalyst in the olefin formation step is not particularly limited so long as it is in the range of from 300 to 700° C., it is preferably from 350 to 600° C. By performing the reaction at a temperature falling within this range, it is possible to prevent a lowering of the selectivity of the olefin.

In addition, the reaction pressure in the olefin formation step is preferably a gauge pressure of 50 kPa or more, more preferably a gauge pressure of 150 kPa or more, still more preferably a gauge pressure of from 150 to 20,000 kPa, and especially preferably a gauge pressure of from 450 to 1,000 kPa. Here, the gauge pressure refers to the pressure expressed on the basis of atmospheric pressure, and the value obtained by adding the atmospheric pressure to the gauge pressure is the absolute pressure.

The contact time between the alcohol and the catalyst is not particularly limited, and for example, in the case of performing calculation while reducing the volume of the raw material used for the reaction into that of a gas at 25° C. and 1 atm, the contact time is from 0.001 seconds to one hour, and preferably from 0.1 seconds to one minute.

In addition, it is preferable that the yield of the olefin whose number of carbon atoms is at least one more than the number of carbon atoms of the alcohol serving as the raw material is higher. The yield of the olefin is preferably 1% or more, more preferably 5% or more, and still more preferably 10% or more.

Here, the yield of the olefin can be determined by {(the number of moles of carbon of the olefin formed, whose number of carbon atoms is at least one more than the number of carbon atoms of the alcohol)/(the number of moles of carbon of the alcohol used for the reaction)×100(%)}.

[3. Polyolefin and Olefin Oxide]

The polyolefin of the present invention is produced by polymerizing the olefin obtained by the previously described method for producing an olefin of the present invention. The polyolefin represented by polypropylene is inexpensive and excellent in mechanical properties, and therefore, it is used as a structural material in a wide field.

Examples of the method for the production of such a polyolefin include a method in which an olefin or an olefin mixture is allowed to react in a gas phase or liquid phase in the presence of a polymerization catalyst; and a method in which after the polymerization to form a single polymer, another olefin or olefin mixture is polymerized. Preferred examples of the polyolefin include a homopolymer of propylene; a random copolymer of propylene and ethylene; and a polypropylene-based composition obtained by producing a homopolymer of propylene in a first step and producing a random copolymer of propylene and ethylene in a second step.

In addition, the olefin oxide of the present invention is produced by, for example, oxidizing the olefin obtained by the previously described method for producing an olefin of the present invention. An olefin oxide represented by propylene oxide is industrially important as an intermediate raw material for industrial chemicals, synthetic resins, rubbers, and the like. Examples of the method for the production of such an olefin oxide include a method in which an olefin is brought into contact with a peroxide in the presence of a catalyst for olefin oxide production; and a method in which a chlorohydrin is produced from an olefin and chlorine, and the chlorohydrin is brought into contact with a base such as calcium hydroxide.

EXAMPLES

Embodiments of the present invention are described in more detail below by illustrating Examples. As a matter of course, the present invention is not limited to the following Examples, and various forms regarding the details can be made.

Example 1

(1) Preparation of Catalyst A

A zirconium oxide powder (RC-100, available from Daiichi Kigenso Kagaku Kogyo Co., Ltd.) was subjected to particle size regulation into a size of from 0.3 to 0.6 mm by means of sieving, thereby obtaining a catalyst for olefin production. This catalyst is hereinafter referred to as "Catalyst A".

Incidentally, it was confirmed from a powder X-ray diffraction pattern of Catalyst A that the crystal structure thereof was a monoclinic crystal.

(2) Production of Propylene 0.50 g of Catalyst A was filled in a quartz tube having a cross-sectional area of 0.85 $cm^2$, and an ethanol/nitrogen mixed gas having an ethanol concentration of 33% by volume was fed at a rate of 11 mL/min into the reaction tube and allowed to react at atmospheric pressure and 400° C. (contact time: 2.8 seconds). A gas discharged from a gas exhaust port of the reaction tube was analyzed by means of gas chromatography to determine the yield and the formation rate of propylene. The analysis results obtained are shown in the following Table 1.

Comparative Example 1

(1) Preparation of Catalyst B

A catalyst in which nickel was supported on a carrier made of silica was prepared according to the method described in WO 2007/083684 A. The preparation of the catalyst was performed according to the following procedures.

306 g of colloidal silica (SNOWTEX (registered trademark) 20, available from Nissan Chemical Industries, Ltd.), 225 g of dodecyl trimethyl ammonium bromide, 71 g of a 4N sodium hydroxide aqueous solution, and 705 g of ion-exchanged water were mixed, and the mixture was heated at 140° C. for 48 hours while allowing it to stand. Subsequently, the resultant was filtered, and a filtration residue was dried, affording a dried material.

8 g of the dried material was add to 80 g of ion-exchanged water, to which was then added a solution of 1.1 g of nickel nitrate hexahydrate dissolved in 81 g of ion-exchanged water, and the mixture was heated at 80° C. for 20 hours. Thereafter, the resultant was filtered, and a filtration residue was dried and heated in air at 550° C., thereby obtaining Ni-MCM41. This catalyst is hereinafter referred to as "Catalyst B".

It was confirmed from a powder X-ray diffraction pattern that the obtained Catalyst B had a hexagonal structure, and the Catalyst B had a BET surface area of 844 $m^2$/g and a nickel concentration of 3.6% by mass.

(2) Production of Propylene

Propylene was produced in the same manner as that in Example 1, except for using Catalyst B in place of the Catalyst A. The results are shown in the following Table 1.

Incidentally, in Table 1, "C3'" denotes propylene (the same applies hereinafter); the yield of "C3' yield" is defined by {(the number of moles of carbon in propylene formed)/(the number of moles of carbon in the alcohol used for the reaction)×100(%)}; and "C3' formation rate" denotes the mass of propylene formed for one hour per mL of the catalyst.

As shown in the foregoing Table 1, in Example 1, the weight (yield) of propylene formed for one hour per mL of the catalyst was greatly large, as compared with Comparative Example 1.

Example 2

(1) Preparation of Catalyst C

A zirconium oxide powder (RSC-HP, available from Daiichi Kigenso Kagaku Kogyo Co., Ltd.) was subjected to particle size regulation into a size of from 0.18 to 0.3 mm by means of sieving, thereby obtaining a catalyst for olefin production. This catalyst is hereinafter referred to as "Catalyst C".

(2) Production of Propylene 1.00 g of Catalyst C was filled in a quartz tube having a cross-sectional area of 0.83 $cm^2$. 3 mL/min of an ethanol gas, 3 mL/min of nitrogen, and 6 mL/min of water as water vapor were fed, respectively into the reaction tube and allowed to react under a gauge pressure of 500 kPa at 450° C.

180 minutes after starting the ethanol feed, a gas discharged from a gas exhaust port of the reaction tube was analyzed by means of gas chromatography to determine the conversion of ethanol and the yield of the product. The results are shown in Table 2.

In Table 2, "EtOH" denotes ethanol; "$H_2O$" denotes water; "C3'" denotes propylene; "C2'" denotes ethylene; "C2" denotes ethane; "C2s" denotes ethylene+ethane; "C3" denotes propane; "C3s" denotes propylene+propane; "C4s" denotes isobutene+1-butene+trans-2-butene+cis-2-butene+1,3-butadiene+n-butane+isobutane; and "BTX" denotes benzene+toluene+o-xylene+m-xylene+p-xylene (the same applies hereinafter).

Incidentally, the yield of each product is defined by {(the number of moles of carbon in each product in the outlet of the reaction tube)/(the number of moles of carbon of ethanol used for the reaction)×100(%)} (hereinafter the same).

The conversion is defined by {1−(number of moles of carbon of ethanol after the reaction)/(number of moles of carbon of ethanol fed)×100(%)} (the same applies hereinafter).

Comparative Example 2

(1) Preparation of Catalyst D

Zr-modified ZSM-5 (80) was fabricated by adopting the method described in *Catalysis Letters* (2009), pp. 364-369.

TABLE 1

| | Catalyst | Catalyst weight (g) | Catalyst volume (mL) | Reaction temperature (° C.) | C3' yield (%) | C3' formation rate (g-C3' $h^{-1}$ mL-$cat^{-1}$) |
| --- | --- | --- | --- | --- | --- | --- |
| Example 1 | Catalyst A | 0.50 | 0.50 | 400 | 13 | 0.066 |
| Comparative Example 1 | Catalyst B | 0.50 | 2.0 | 400 | 10 | 0.013 |

Specifically, 3 g of NH$_4$ type ZSM-5 (CBV8014, available from Zeolyst International, Inc.) was added to an aqueous solution of ZrO(NO$_3$)$_2$.2H$_2$O (0.13 g) dissolved in 40 mL of pure water (zirconium/aluminum molar ratio=0.4), and the mixture was dried at 50° C. by an evaporator and further dried at 100° C. for 5 hours. Thereafter, the resultant was calcined in air at 540° C. for 4 hours, affording Zr-modified ZSM-5 (80).

The Zr-modified ZSM-5 (80) was subjected to particle size regulation into a size of from 0.18 to 0.3 mm by means of sieving, thereby obtaining a catalyst for olefin production. This catalyst is hereinafter referred to as "Catalyst D". A zirconium concentration in Catalyst D was 1.5% by weight. Incidentally, since Catalyst D has a surface area of 431 m$^2$/g and a zirconium concentration of 1.5% by weight, assuming that zirconium oxide forms a monomolecular layer (in that case, the area becomes maximum), the surface area of zirconium oxide contained in 1 g of Catalyst D will become not more than 21 m$^2$, namely the surface area of zirconium oxide will become not more than 5% of the surface area of Catalyst D according to calculations.

(2) Production of Propylene

The same operations as those in Example 2 were followed, except for using 1.00 g of Catalyst D, and the conversion of ethanol and the yield of the product were determined. The results are shown in the following Table 2.

Comparative Example 3

(1) Preparation of Catalyst E 0.50 g of spherical alumina (KHO-12, available from Sumitomo Chemical Co., Ltd.) was pulverized and classified into a size of from 0.3 to 0.6 mm, thereby obtaining a catalyst for olefin production. This catalyst is hereinafter referred to as "Catalyst E".

(2) Production of Propylene

Catalyst E was filled in a quartz tube having a cross-sectional area of 0.85 cm$^2$, and an ethanol/nitrogen mixed gas having an ethanol concentration of 33% by volume was fed at a rate of 11 mL/min into the reaction tube and allowed to react at atmospheric pressure and 450° C. A gas discharged from a gas exhaust port of the reaction tube was analyzed by means of gas chromatography to determine the conversion of ethanol and the yield of each product. The results are shown in the following Table 2.

Example 3

1.02 g of Catalyst C was filled in a quartz tube having a cross-sectional area of 0.071 cm$^2$. 2 mL/min of an ethanol gas, 2 mL/min of nitrogen, and 0 mL/min, 2 mL/min, 10 mL/min, 20 mL/min, or 30 mL/min of water as water vapor were fed, respectively into the reaction tube and allowed to react at atmospheric pressure and 410° C. A gas discharged from a gas exhaust port of the reaction tube was analyzed by means of gas chromatography to determine the conversion of ethanol and the yield of propylene. The results are shown in the following Table 3.

TABLE 3

| Total flow rate (mL/min) | Flow rate of EtOH (mL/min) | Flow rate of H$_2$O (mL/min) | H$_2$O/EtOH ratio (mol/mol) | Conversion (%) | C3' yield (%) |
|---|---|---|---|---|---|
| 6 | 2 | 0 | 0 | 100 | 9.6 |
| 8 | 2 | 2 | 1 | 100 | 19.0 |
| 16 | 2 | 10 | 5 | 100 | 25.0 |
| 26 | 2 | 20 | 10 | 97.0 | 21.3 |
| 36 | 2 | 30 | 15 | 83.0 | 10.8 |

From Table 3, the C3' (propylene) yield became high with an increase of the ratio of water. As a result, taking the results of the conversion into consideration, it may be considered that the case where the H$_2$O/EtOH ratio is in the vicinity of 5 is most practically useful.

Example 4

1.02 g of Catalyst C was filled in a quartz tube having a cross-sectional area of 0.071 cm$^2$. 3 mL/min of an ethanol gas, 6 mL/min of nitrogen, and 3 mL/min of water as water vapor were fed, respectively into the reaction tube and allowed to react under a gauge pressure of 0 kPa, 100 kPa, 200 kPa, or 500 kPa at 450° C. A gas discharged from a gas exhaust port of the reaction tube was analyzed by means of gas chromatography to determine the conversion of ethanol and the yield of propylene. The results are shown in the following Table 4.

Example 5

The same operations as those in Example 4 were followed, except that 3 mL/min of an ethanol gas, 3 mL/min

TABLE 2

| | Catalyst | Reaction pressure (kPaG) | H$_2$O/EtOH (mol/mol) | Conversion (%) | C3'/C3s | C2'/C2s | Yield/(%) (C-mol base) | | | | | | |
|---|---|---|---|---|---|---|---|---|---|---|---|---|---|
| | | | | | (mol/mol) | | C2' + C3' | C3' | C3 | C2' | C2 | C4s | BTX |
| Example 2 | Catalyst C | 500 | 2 | 100 | 0.998 | 0.996 | 84.6 | 31.9 | 0.1 | 52.7 | 0.2 | 0.3 | 0.03 |
| Comparative Example 2 | Catalyst D | 500 | 2 | 100 | 0.036 | 0.153 | 2.1 | 1.2 | 32.4 | 0.9 | 5.0 | 13.2 | 27.27 |
| Comparative Example 3 | Catalyst E | 0 | 0 | 100 | 0.997 | 0.998 | 92.5 | 1.1 | 0.004 | 91.4 | 0.2 | 2.8 | Not measured |

As compared with Catalyst D in which the surface is not substantially constituted of zirconium oxide and Catalyst E that is a solid acid catalyst, Catalyst C which corresponds to the present invention was high in the selectivity to an olefin whose number of carbon atoms is at least one more than the number of carbon atoms of ethanol.

of nitrogen, and 6 mL/min of water as water vapor were fed, respectively into the reaction tube and that the reaction pressure was 500 kPa in terms of a gauge pressure, and the conversion of ethanol and the yield of propylene were determined. The results are shown in the following Table 4.

TABLE 4

|  | Reaction pressure (kPaG) | Total flow rate (mL/min) | Flow rate of EtOH (mL/min) | Flow rate of H$_2$O (mL/min) | H$_2$O/EtOH ratio (mol/mol) | Conversion (%) | C3' yield (%) |
|---|---|---|---|---|---|---|---|
| Example 4 | 0 | 12 | 3 | 3 | 1 | 100 | 14.2 |
|  | 100 | 12 | 3 | 3 | 1 | 100 | 17.4 |
|  | 200 | 12 | 3 | 3 | 1 | 100 | 19.3 |
|  | 500 | 12 | 3 | 3 | 1 | 100 | 23.6 |
| Example 5 | 500 | 12 | 3 | 6 | 2 | 100 | 29.2 |

From Table 4, the higher the gauge pressure, the higher the C3' (propylene) yield was. Then, by increasing the H$_2$O/EtOH ratio, the C3' (propylene) yield became higher (Example 5).

Example 6

(1) Preparation of Catalyst F 26.2 g of zirconium oxychloride octahydrate was dissolved in 60.1 g of pure water, and 30% ammonia water was added until the pH of the solution reached 3. The solution was stirred for one hour, affording a zirconium oxide precursor-containing precipitate in a gel form. The zirconium oxide precursor-containing precipitate was recovered from the solution by means of filtration and washed with 200 mL of pure water. The washed zirconium oxide precursor-containing precipitate was heated in air at 110° C. for 12 hours and then at 450° C. for 3 hours, thereby obtaining calcined zirconium oxide. The calcined zirconium oxide was pulverized and subjected to particle size regulation into a size of from 0.3 to 0.6 mm by means of sieving. Thereafter, the resultant was rinsed with pure water and dried at 110° C. until the weight did not change, thereby obtaining dried zirconium oxide. The dried zirconium oxide was pulverized and subjected to particle size regulation into a size of from 0.18 to 0.3 mm by means of sieving, thereby obtaining a catalyst for olefin production. This catalyst is hereinafter referred to as "Catalyst F". X-ray diffraction measurement found that Catalyst F was zirconium oxide of a tetragonal crystal.

(2) Production of Propylene 0.50 g of Catalyst F was filled in a quartz tube having a cross-sectional area of 0.071 cm$^2$. 3 mL/min of an ethanol gas, 6 mL/min of nitrogen, and 3 mL/min of water as water vapor were fed, respectively into the reaction tube and allowed to react under a gauge pressure of 200 kPa at 450° C. A gas discharged from a gas exhaust port of the reaction tube was analyzed by means of gas chromatography to determine the conversion of ethanol and the yield of propylene. The results are shown in the following Table 5. In comparison with Example 4 using Catalyst C which is zirconium oxide of a monoclinic crystal, in the case of using Catalyst F which is zirconium oxide of a tetragonal crystal, the propylene yield was high while the catalyst amount was a half.

INDUSTRIAL APPLICABILITY

The present invention can be suitably utilized in the field of the production of chemical raw materials, in particular the field of the production of olefins capable of serving as raw materials for polyolefins and olefin oxides.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for producing propylene from ethanol including a propylene formation step wherein ethanol is brought into contact with a catalyst at a temperature of from 300° C. to 700° C. and at a gauge pressure of 50 kPa or more, wherein an area ratio of zirconium oxide on a surface of the catalyst is 50% by area or more, the propylene yield on a carbon mol basis is 9.6% or more, and wherein a yield of other hydrocarbons having 4 or more carbon atoms is less than 13.2%, and wherein the ethanol contains water in an amount of 1 to 10 molar times the molar number of the ethanol.

2. The method for producing propylene according to claim 1, wherein the ethanol contains water in an amount of not more than 7 molar times the molar number of the ethanol.

3. The method for producing propylene according to claim 1, wherein the ethanol is brought into contact with the catalyst at a gauge pressure of 100 kPa or more.

4. The method for producing propylene according to claim 1, wherein the ethanol is brought into contact with the catalyst at a gauge pressure of 150 kPa or more.

5. The method for producing propylene according to claim 1, wherein the ethanol is brought into contact with the catalyst at a gauge pressure of from 150 to 20,000 kPa.

TABLE 5

|  | Reaction pressure (kPaG) | Total flow rate (mL/min) | Flow rate of EtOH (mL/min) | Flow rate of H$_2$O (mL/min) | H$_2$O/EtOH ratio (mol/mol) | Conversion (%) | C3' yield (%) |
|---|---|---|---|---|---|---|---|
| Example 6 | 200 | 12 | 3 | 3 | 1 | 100 | 21.3 |

6. The method for producing propylene according to claim 1, wherein the ethanol is brought into contact with the catalyst at a gauge pressure of from 450 to 1000 kPa.

7. The method for producing propylene according to claim 1, wherein the ethanol contains water in an amount of 5 to 10 molar times the molar number of the ethanol.

\* \* \* \* \*